United States Patent [19]
Ueno et al.

[11] Patent Number: 5,185,374
[45] Date of Patent: Feb. 9, 1993

[54] USE OF 15-KETOPROSTAGLANDIN E OR F COMPOUNDS FOR UTERINE CONTRACTION

[75] Inventors: Ryuzo Ueno; Ryuji Ueno; Tomio Oda, all of Hyogo, Japan

[73] Assignee: K.K. Ueno Seiyaku Oyo Kenkyujo, Osaka, Japan

[21] Appl. No.: 687,790

[22] Filed: Apr. 22, 1991

Related U.S. Application Data

[63] Continuation of Ser. No. 349,548, May 9, 1989, abandoned.

[30] Foreign Application Priority Data

May 11, 1988 [JP] Japan ................... 63-115408
Jun. 2, 1988 [JP] Japan ................... 63-137666

[51] Int. Cl.$^5$ ................... A61K 31/19; A61K 31/557; C01C 61/06
[52] U.S. Cl. ................... 514/570; 514/530; 514/573; 562/503
[58] Field of Search ................... 514/530, 573, 570; 562/503

[56] References Cited

U.S. PATENT DOCUMENTS

3,978,229  8/1976  Matsumoto et al. ............ 514/530
4,576,962  3/1986  Matthews ...................... 514/530

FOREIGN PATENT DOCUMENTS

0153858  9/1985  European Pat. Off. .
1171154  11/1966  United Kingdom .
1186505  5/1967  United Kingdom .
1476661  5/1974  United Kingdom .
1554044  1/1977  United Kingdom .
2001636  7/1978  United Kingdom .

OTHER PUBLICATIONS

European Search Report dated Jul. 19, 1989.
Research Disclosure, Aug. 1978, No. 172115, pp. 92-93.
Research Disclosure, Ibid, Aug. 1978, No. 172116, p. 56.
Chemical Abstract, vol. 83, (1975), 108983, pp. 107-108.
Chemical Abstract, vol. 104, (1986), 46297, p. 111.
Chemical Abstract, vol. 81, (1974), 45774, p. 69.
Acta Physiol. Scand., vol. 66, (1966), pp. 509-510.
Publication entitled "Prostaglandins and Related Substances", (1983), pp. 11-15.
Publication, M. Bygdeman et al., Life Science, vol. 14, (1974), pp. 521-531.
Publication, W. L. Miller et al., Prostaglandins, vol. 9, (1975), pp. 9-18.
Publication, J. W. Wilks, Prostaglandins, vol. 13, (1977), pp. 161-170.

*Primary Examiner*—Leonard Schenkman
*Attorney, Agent, or Firm*—Sughrue, Mion, Zinn, Macpeak & Seas

[57] ABSTRACT

A method of inducing uterine contraction which comprises administering, to a subject in need of such contraction, a uterine-contractionally effective amount of a prostanoic acid derivative selected from the group consisting of
a) 15-ketoprostaglandin E compounds, and
b) 15-ketoprostaglandin F compounds with the proviso that when the only one group, which is unsubstituted n-pentyl group, is attached to the carbon atom at the 15-position of the prostanoic acid nucleus and the bond between the carbon atoms at 5- and 6-positions is a double bond, then the bond between the carbon atoms at 13- and 14-positions is a single bond.

22 Claims, No Drawings

USE OF 15-KETOPROSTAGLANDIN E OR F COMPOUNDS FOR UTERINE CONTRACTION

This is a Continuation of Application No. 07/349,548 filed May 9, 1989 abandoned.

BACKGROUND OF THE INVENTION

1. Field of the Invention

The present invention relates to a use of 15-keto-prostaglandin E or F compounds for uterine contraction.

Prostaglandins (hereinafter, prostaglandin is referred to as PG ) are members of a class of organic carboxylic acid that are contained in human and most other mammalian tissues or organs and that exhibit a wide range of physiological activities. Naturally occurring PGs possess as a common structural feature the prostanoic acid skeleton:

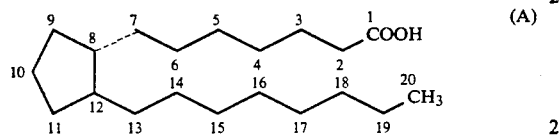

(A)

while some of synthetic analogues have somewhat modified skeletons. The natural PGs are classified based on the structual feature of five-membered cycle moiety into PGAs, PGBs, PGCs, PGDs, PGEs, PGFs, PGGs, PGHs, PGIs and PGJs, and also on the presence or absence of unsaturation and oxidation in the chain moiety as:

Subscript 1—15—OH
Subscript 2—5,6-unsaturated—15—OH
Subscript 3—5,6— and 17, 18-diunsaturated—

Further, PGFs are sub-classified according to the configration of hydroxy groups at 9- and 11-position into α(both hydroxy groups being in alpha configration) and β(both hydroxy groups being in beta configration).

2. Background Information

Natural $PGE_1$, $PGE_2$ and $PGE_3$ are known to have vasodilating, hypotensive, gastro-juice reducing, intestine-hyperkinetic, uterine contracting, diuretic, bronchodilating and anti-ulcer activities. Also, natural $PGF_{1\alpha}$, $PGF_{2\alpha}$ and $PGF_{3\alpha}$ are known to have hypertensive, vasocontracting, intestine-hyperkinetic, uterine contacting, luteo-regressive and bronchocontracting activities. Among others, $PGF_{2\alpha}$ is put into practical use as parturifacient and also is known to have anti-pregnant activity. However, application of $PGF_{2\alpha}$ is limited by its undersirable side-effects, i.e. intestine-contracting and intraocular hypertensive activities.

In addition, some 15-keto (i.e. having an oxo group at. 15-position in place of the hydroxy group) prostaglandins and 13,14-dihydro-15-keto-prostaglandins are known as substances naturally produced by enzymatic actions during metabolism of natural PGs (Acta Physiologica Scandinavica, 66, 509, 1966). It has also been described that 15-keto-prostaglandin $F_{2\alpha}$ has an anti-pregnant activity.

SUMMARY OF THE INVENTION

In the first aspect, the present invention provides a method of inducing uterine contraction which comprises administering, to a subject in need of such contraction, a uterine-contractionally effective amount of a prostanoic acid derivative selected from the group consisting of a) 15-keto-prostaglandin E compounds, and
b) 15-keto-prostaglandin F compounds with the proviso that when the only one group, which is unsubstituted n-pentyl group, is attached to the carbon atom at the 15-position of the prostanoic acid nucleus and the bond between the carbon atoms at 5- and 6-positions is a double bond, then the bond between the carbon atoms at 13- and 14-positions is a single bond.

In the second aspect, the present invention provides a use of prostanoic acid derivative as defined above for the manufacture of a medicament for inducing uterine contraction.

In the third aspect, the present invention provides a pharmaceutical composition for inducing uterine contraction comprising a prostanoic acid derivative as defined above in association with a pharmaceutically acceptable carrier, diluent or excipient.

At least in some cases, interruption of pregnancy is attributed to uterine contraction.

DETAILED DESCRIPTION OF THE INVENTION

As used herein, the term "uterine contraction" refers to the contraction of a part or the whole of uterine and usually of myometrium.

The term "interruption of pregnancy" refers to artificial interruption of pregnancy or abortion usually from fecundation or nidation to early or middle stage of pregnancy.

The term "15-keto-prostaglandin E compounds", referred to as 15-keto-PGE compounds, include any prostaglandin E derivatives which have an oxo group in place of the hydroxy group at 15-position of the prostanoic acid nucleus irrespective of the presence or absence of the double bond between 13- and 14-positions.

The term "15-keto-prostaglandin F compounds", referred to as 15-keto-PGF compounds, include any prostaglandin F derivatives which have an oxo group in place of the hydroxy group at 15-position of the prostanoic acid nucleus irrespective of the presence or absence of the double bond between 13- and 14-positions.

Nomenclature

Nomenclature of 15-keto-PGE or F compounds herein uses the numbering system of prostanoic acid represented in the formula (A) shown above.

While the formula (A) shows a basic skeleton having twenty carbon atoms, the 15-keto-PGE compounds and 15-keto-PGF compounds used in the present invention are not limited to those having the same number of carbon atoms. The carbon atoms in the Formula (A) are numbered 2 to 7 on the α-chain starting from the α-carbon atom adjacent to the carboxylic carbon atom which is numbered 1 and towards the five-membered ring, 8 to 12 on the said ring starting from the carbon atom on which the α-chain is attached, and 13 to 20 on the ω-chain starting from the carbon atom adjacent to the ring. When number of carbon atoms is decreased in the α-chain, the number is deleted in order starting from 2-position and when number of carbon atoms is increased in the α-chain, compounds are named as substituted derivatives having respective substituents at 1-position in place of carboxy group (C-1). Similarly, when number of carbon atoms is decreased in the ω-chain, the number is deleted in order starting from 20-position and when number of carbon atoms is increased in the ω-chain, compounds are named as substituted derivatives having respective substituents at 20 position. Stereochemistry of compounds is the same as that of the above formula (A) unless otherwise specified. Thus, 15-keto-PGEs having 10 carbon atoms in the ω-chain is nominated as 15-keto-20-ethyl-PGEs.

The above formula expresses a specific configuration which is most typical one, and in this specification compounds having such a configuration are expressed without any specific indication about it.

PGEs have a hydroxy group on the carbon atom at 11-position in general, but in the present specification the term "PGEs" includes PGs having other group than hydroxyl group at 11-position. Such PGEs are called as 11-dehydroxy-11-substituted-PGEs, for instance, as 11-dehydroxy-11-methyl-PGEs where the substituent is a methyl group. The same is applied also to PGFs.

Although PGEs and PGFs are generally refers to compounds having a hydroxy group at 11-position of the prostanoic acid nucleus, the 15-keto-prostaglandin E compounds and 15-keto-prostaglandin F compounds in the present invention are extended to include compounds having another group at 11-position. Such compounds are named as 11-dehydroxy-11-substituted compounds.

As stated above, nomenclature of 15-keto-PGE or F compounds is based upon the prostanoic acid. These compounds, however, can also be named according to the IUPAC naming system. For example, 13,14-dihydro-15-keto-16R,S-fluoro-PGE$_2$ is (Z)-7-{(1R,2R,3R)-3-hydroxy-2-[(4R,S)-4-fluoro-3-oxo-cyclopentyl]-hept-5-enic acid. 13,14-dihydro-15-keto-20-ethyl-11-dehydroxy-11R-methyl-PGE$_2$ methyl ester is methyl 7-{(1R,2S,3R)-3-methyl-2-[3-oxo-1-decyl]-5-oxo-cyclopentyl}-hept-5-enoate. 13,14-dihydro-6,15-diketo-19-methyl-PGE$_1$ ethyl ester is ethyl 7-{(1R,2R,3R)-3-hydroxy-2-(7-methyl-3-oxo-1-octyl)-5-oxo-cyclopentyl)-6-oxo-heptanoate. 13,14-dihydro-15-keto-20-ethyl-PGF$_{2\alpha}$ isopropyl ester is isopropyl (Z)-7-[(1R,2R,3R,5S)-3,5-dihydroxy-2-(3-oxo-1-nonyl)-cyclopentyl}-hept-5-enoate.

Preferred Compounds

The 15-keto-PGE compounds used in the present invention may be any derivatives of PGE in so far as they have an oxo group at 15 position in place of the hydroxy group, and may have a single bond (15-keto-PGE$_1$ compounds), a double bond (15-keto-PGE$_2$ compounds) between 5- and 6-positions, or two double bonds (15-keto-PGE$_3$ compounds) between 5- and 6- positions as well as 17- and 18-positions.

Similarly, 15-keto-PGF$_2$ compounds may be 15-keto-PGF$_1$ compounds, 15-keto-PGF$_2$ compounds or 15-keto-PGF$_3$ compounds (with α- and β-types inclusive).

Typical examples of the compounds used in the present invention are 15-keto-PGE$_1$, 15-keto-PGE$_2$, 15-keto-PGE$_3$, 13,14-dihydro-15-keto-PGE$_1$, 13,14-dihydro-15-keto-PGE$_2$, 13,14-dihydro-15-keto-PGE$_3$, 15-keto-PGF$_1$, 15-keto-PGF$_2$, 15-keto-PGF$_3$, 13,14-dihydro-15-keto-PGF$_1$, 13,14-dihydro-15-keto-PGF$_2$, 13,14-dihydro-15-keto-PGF$_3$ and so on as well as their derivatives.

Said derivatives include esters at the carboxy group at the alpha chain, pharmaceutically acceptable salts, unsaturated derivatives having a double bond or a triple bond between 2- and 3-positions or 5- and 6-positions, respectively, substituted derivatives having substituent(s) on carbon atom(s) at 3-, 6-, 16-, 17-, 19- and/or 20-position and compounds having lower alkyl or a hydroxy (lower) alkyl group at 11-position in place of the hydroxy group.

Examples of substituents present in preferred compounds are as follows: Substituents on the carbon atom at 3-, 17- and/or 19-position include lower alkyl, for example, $C_{1-4}$ alkyl, especially methyl and ethyl. Substituents on the carbon atom at 16-position include lower alkyl such as methyl, ethyl etc., hydroxy and halogen atom such as chlorine, fluorine, aryloxy such as trifluoromethylphenoxy (which is preferred because of high activity) etc. Substituents on the carbon atom at 20-position include saturated and unsaturated lower alkyl such as C1-4 alkyl, lower alkoxy such as $C_{1-4}$ alkoxy and lower alkoxy (lower) alkyl such as $C_{1-4}$ alkoxy-$C_{1-4}$ alkyl. Substituents on the carbon atom at 6-position include oxo group forming carboxyl. Stereochemistry of PGs having hydroxy, lower alkyl or lower (hydroxy) alkyl substituent on the carbon atom at 9- and/or 11-position may be aplha, beta or a mixture thereof.

Said derivatives may have alkoxy, phenoxy or phenyl group at the end of the omega chain where the chain is shorter than the natural PGs.

Especially preferred compounds are those having a lower alkyl such as methyl, ethyl etc., a halogen atom such as chloro, fluoro etc. at 16-position, those having a lower alkyl such as methyl, ethyl etc. at 20-position, and those having phenyl or phenoxy which are optionally substituted with halogen or haloalkyl at 16-position in place of the rest of chain as these compounds have an enhanced uterine contracting activity.

A group of preferred compounds used in the present invention has the formula (I)

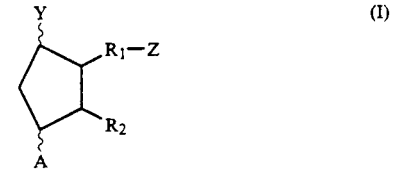

wherein A is hydrogen, hydroxy, halo, lower alkyl or hydroxy(lower)alkyl, Y is a group of A defined as above or oxo, with the proviso that at least one of A and Z is a group other than hydrogen, Z is —CH$_2$OH, —COCH$_2$OH, —COOH or its functional derivative, R$_1$ is bivalent saturated or unsaturated, lower or medium aliphatic hydrocarbon residue which is unsubstituted or substituted with oxo or aryl, R$_2$ is saturated or unsaturated, lower or medium aliphatic hydrocarbon residue which is unsubstituted or substituted with oxo, hydroxy, halo, lower alkoxy, lower alkanoyloxy, cyclo(lower)alkyl, aryl or aryloxy, with the proviso that when A and Y are both hydroxy, R$_1$—Z is —CH$_2$CH=CH(CH$_2$)$_3$COOH and R$_2$ is 3-hydroxy-hydrocarbyl group having eight carbon atoms, then the bond between the α and β carbon atoms of R$_2$ is a single bond.

In the above formula, the term "unsaturated" in the definitions for R$_1$ and R$_2$ is intended to include at least one and optionally more them one double bond and/or triple bond isolatedly, separetely or serially present between carbon atoms of main and/or side chain. According to usual nomenclature, an unsaturation between two serial positions is represented by denoting younger number of said two positions, and an unsaturation between two distal positions is represented by denoting both of the positions. Preferred unsaturation is a double bond at 2-position and a double or triple bond at 5-position.

The term "lower or medium aliphatic hydrocarbon residue" refers to a straight or branched chain hydrocarbyl group having 1 to 14 carbon atoms (for a side chain, 1 to 3 carbon atoms being preferred) and preferably 2 to 8 carbon atoms for $R_1$ and 6 to 12 carbon atoms for $R_2$.

The term "halo" denotes fluoro, chloro, bromo and iodo.

The term "lower" is intended to include a group having 1 to 6 carbon atoms unless otherwise specified.

The term "lower alkyl" as a group or a moiety in hydroxy(lower)alkyl includes saturated and straight or branched chain hydrocarbon radicals containing 1 to 6, preferably 1 to 5 and more preferable 1 to 4 carbon atoms, such as methyl, ethyl, propyl, isopropyl, butyl, isobutyl, t-butyl, pentyl and hexyl.

The term "lower alkoxy" refers to the group loweralkyl-O-phenyl wherein lower alkyl is as defined above.

The term "hydroxy(lower)alkyl" refers to alkyl as defined above and substituted with at least one hydroxy group, such as hydroxymethyl, 1-hydroxyethyl, 2-hydroxyethyl and 1-methyl-1-hydroxyethyl.

The term "lower alkanoyloxy" refers to a group of the formula: RCO-O- wherein RCO- is an acyl group formed by oxidation of a lower alkyl group as defined above, e.g. acetyl.

The term "cyclo(lower)alkyl" refers to a cyclic group formed by cyclization of a lower alkyl group as defined above.

The term "aryl" includes unsubstituted or substituted aromatic carbocyclic or heterocyclic (preferably monocyclic) groups, e.g. phenyl, tolyl, xylyl and thienyl. Examples of substituents are halo and halo(lower) alkyl wherein halo and lower alkyl being as defined above.

The term "aryloxy" refers to a group of the formula: ArO- wherein Ar is aryl as defined above.

The term "functional derivative" of carboxy as X includes salts (preferably pharmaceutically acceptable salts), esters and amides.

Suitable "pharmaceutically acceptable salt" includes conventional non-toxic salt, and may be a salt with an inorganic base, for example a metal salt such as an alkali metal salt (e.g. sodium salt, potassium salt, etc.) and an alkaline earth metal salt (e.g. calcium salt, magnesium salt, etc.), ammonium salt, a salt with an organic base, for example, an amine salt (e.g. methylamine salt, dimethylamine salt, cyclohexylamine salt, benzylamine salt, piperidine salt, ethylenediamine salt, ethanolamine salt, diethanolamine salt, triethanolamine salt, tris(hydroxymethylamino)methane salt, monomethyl-monoethanolamine salt, procaine salt, caffeine salt, etc.), a basic amino acid salt (e.g. arginine salt, lysine salt, etc.) and the like. These salts can be prepared by the conventional process, for example from the corresponding acid and base or by salt interchange.

Examples of the esters are aliphatic esters, for example, $C_{1-6}$ alkyl ester such as methyl ester, ethyl ester, propyl ester, isopropyl ester, bytyl ester, isobutyl ester, t-butyl ester, pentyl ester, 1-cyclopropylethyl ester, etc., lower alkenyl ester such as vinyl ester, allyl ester, etc., lower alkynyl ester such as ethynyl ester, propynyl ester, etc., hydroxy(lower) alkyl ester such as hydroxyethyl ester, lower alkoxy(lower)-alkyl ester such as methoxymethyl ester, 1-methoxyetyl ester, etc., and aromatic esters, for example, optionally substituted aryl ester such as phenyl ester, tolyl ester, t-butylphenyl ester, salicyl ester, 3,4-di-methoxyphenyl ester, benzamidophenyl ester etc., aryl(lower)alkyl ester such as benzyl ester, trityl ester, benzhydryl ester ester, etc. Examples of the amides are mono- or di- lower alkyl amides such as methylamide, ethylamide, dimethylamide, etc., arylamide such as anilide, toluidide, and lower alkyl- or aryl-sulfonylamide such as methlsulfonylamide, ethylsulfonylamide, tolylsulfonylamide etc.

Preferred example of Z include —COOH, —COOCH3, —COOCH —COOCH(CH3)2 and —CONHSO2CH3, Examples of preferred $R_1$ are —(CH$_2$)$_2$—, —(CH$_2$)$_6$—, —CH$_2$CO(CH$_2$)$_2$—, —CH$_2$CH=CH(CH$_2$)$_3$—, —CH$_2$CO(CH$_2$)$_4$—, —(CH$_2$)$_2$CH=CH(CH$_2$)$_2$—, —(CH$_2$)$_4$CH=CH—, —CH$_2$CH=C=CH(CH$_2$)$_2$— etc.

Examples of preferred $R_2$ are —(CH$_2$)$_2$CO(CH$_3$, —(CH$_2$)$_2$CO(CH$_2$)$_4$—COOH, —(CH$_2$)$_2$COC(CH$_3$)$_2$(CH$_2$)$_3$—CH$_3$, —(CH$_2$)$_2$COCH$_2$O—phenyl, —(CH$_2$)$_2$COCHO$_2$-methachlorophenyl, —(CH$_2$)$_2$COCH$_2$O-methatrifluorophenyl, —(CH$_2$)$_2$COCH$_2$O—3-thienyl, —(CH$_2$)$_2$CO(CH$_2$)$_2$-phenyl, —(CH$_2$)$_2$COCH$_2$CH(CH$_3$)(CH$_2$)CH$_3$, —(CH$_2$)$_2$COC(CH$_3$)$_2$CH$_2$OCH$_2$CH$_3$, —(CH$_2$)$_2$COCH(CH=CH) (CH$_2$)$_3$CH$_3$, —(CH$_2$)$_2$CO-cyclopentyl, —(CH$_2$)$_2$CO-cyclohexyl, —(CH$_2$)$_2$CO(CH$_2$)$_2$-cyclohexyl, —(CH$_2$)$_2$COCH$_2$CH(CH$_3$)(CH$_2$)CH=C—(CH$_3$)$_2$, —(CH$_2$)$_2$COCH(CH$_3$)CH$_2$CC=CH, —CH=CHCO(CH$_2$)$_4$—CH$_3$, —CH=CHCOC(CH$_3$)$_2$(CH$_2$)$_3$—CH$_3$, —CH=CHCOCH$_2$O-phenyl, —CH=CHCO—CH$_2$O-methachlorophenyl, —CH=CHCOCH$_2$O-methatrifluorophenyl, —CH=CHCOCH$_2$O-3-thienyl, —CH=CHCO(CH$_2$)$_2$-phenyl, —CH=CH-COCH$_2$CH(CH$_3$)CH$_2$)$_3$CH$_3$, —CH=CH-COC(CH$_3$)$_2$CH$_2$OCH$_2$CH$_3$, —CH=CH-COCH(CH=CH)(CH$_2$)$_3$CH$_3$, —CH=CHCO-cyclopentyl, —CH=CHCO-cyclohexyl, —CH=CH-COCH$_2$CH(CH$_3$)(CH$_2$)$_2$CH=C(CH$_3$)$_2$, —CH=CH-COCH(CH$_3$)CH$_2$CC=CH, —CH=CHCH$_2$COCH(CH$_3$)(CH$_2$)$_4$CH$_3$ etc.

The configration of the ring and α- and/or omega chain in the above formula (I) may be the same as or different from that in the natural prostaglandins. However, the present invention also include a mixture of a compound having natural configuration and that of unnatural configuration.

Examples of the typical compounds of the present invention are 15-keto-PGE and 13,14-dihydro-15-keto-PGE and their derivatives such as 6-keto-derivatives, Δ$^2$-derivatives, 3R,S-methyl-derivatives, 16R,S-methyl-derivatives, 16,16-dimethyl-derivatives, 16R,S-fluoro-derivatives, 16,16-difluoro-derivatives, 17S-methyl-derivatives, 19-methyl-derivatives, 20-methylderivatives and 16-desbutyl-16-trifluoromethylphenoxy derivateves of 15-keto-PGEs, 13,14-dihydro-15-keto-PGEs, 15-keto-PGEs, 15-keto-PGFs and 13,14-dihydro-15-keto-PGFs.

Some of the compounds used in the present invention are novel and may be prepared by the method disclosed in Japanese Patent Application No. 18326/1988 and 108329/1988. Alternatively, these compounds may be prepared by a process analogous to that described herein or to known process.

A practical preparation of the 13,14-dihydro-15-keto compounds involves the following steps; referring to the synthetic charts(I) to (III), reaction of the aldehyde (2) prepared by the Collins oxidation of commercially available (−)-Corey lactone (1) with dimethyl (2-oxoheptyl)-phosphate anion to give α,β-unsaturated ketone (3), reduction of the α,β-unsaturated ketone (3) to the corresponding saturated ketone (4), protection of the carbonyl group of the ketone (4) with a diol to the corresponding ketal (5), and deprotection of the p-phenylbenzoyl group to give the corresponding alcohol (6) followed by protection of the newly derived hydroxy group with dihydropyrane to give the corresponding tetrahydropyranyl ether (7). According to the above process, a precursor of PGEs wherein ω-chain is a 13,14-dihydro-15-keto-alkyl group is prepared.

Using the above tetrahydropyranyl ether (7), 6-keto-PGE$_1$s (15) of which a group constituted with carbon atoms of 5-, 6- and 7-position is —CH$_2$—C(O)—CH$_2$—, may be prepared in the following steps; reduction of the tetrahydropyranyl ether (7) with, for example, diisobutyl aluminum hydride to give the corresponding lactol (8), reaction of the lactol (8), with the ylide generated from (4-carboxybutyl)triphenyl phosphonium bromide followed by esterification (10), cyclization between the 5,6-double bond and the hydroxyl group at 9-position with NBS or iodine to give the halogenated compound (11), dehydrohalogenation of the compound (11) with, for example, DBU to give the 6-keto compound (13) followed by Jones oxidation and removal of the protecting groups.

Furthermore, PGE$_2$s (19) of which a group constituted with carbon atoms of 5-, 6- and 7-position is —CH$_2$—CH=CH— may be prepared in the following steps; as shown in the synthetic chart II, reduction of the above tetrahydropyranyl ether (7) to give the lactol (8), reaction of the resultant lactol (8) with the ylide derived from (4-carboxybutyl-)triphenyl phosphonium bromide to give the carboxylic acid (16) followed by esterification to give ester (17), Jones oxidation of the esters (17) to give the compound (18), and removal of the protecting groups.

Using the above the tetrahydropyranyl ether (7) as the starting material, the compound having —CH$_2$—CH$_2$—CH$_2$— may be prepared by using the same process as that for preparing PGE$_2$ having —CH$_2$CH=CH— and subjecting the resultant compound (18) to catalytic reduction for reducing the double bond between the 5- and 6-positions followed by removal of the protective groups.

Synthesis of 5,6-dehydro-PGE$_2$s having —CH$_2$—C≡C— may be carried out by capturing a copper enolate formed by 1,4-addition of a monoalkylcopper complex or a dialkylcopper complex of the following formulae:

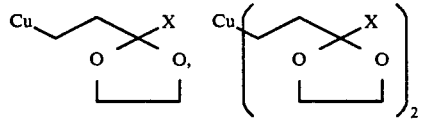

to 4R-t-butyldimethylsilyloxy-2-cyclopenten-1-one with 6-alkoxycarbonyl-1-iodo-2-hexyne or the derivatives.

The 11-β type PGEs can be prepared according to the synthetic chart III.

Corresponding PGF compounds can be produced analogously.

PGE derivatives having methyl group at 11-position in place of hydroxy can be prepared by reacting a dimethyl copper complex with PGA-type compound obtained by subjecting 9-hydroxy-11-tosylate to the Jones oxidation. Alternatively, they can be prepared by protecting carbonyl of saturated ketone (4) produced by reduced by reducing unsaturated ketone (3), eliminating p-phenylbenzoyl and tosylating the produced alcohol, treating with DBU to form a lactol, introducing the alpha-chain by Wittig reaction, oxidizing the alcohol at 9-position to give PGA-type compound, and reacting the product with dimethyl copper complex in order to introduce a methyl group into 11-position to give 11-methyl-PGE-type compound, which on reduction with e.g. sodium borohydride gives 11-methyl-PGF-type compound. 11-hydroxymethyl-PGE-type compound, is obtained by a benzophenone-sensitized photoaddition of methanol of PGA-type compound, which is reduced with e.g. sodium borohydride to give 11-hydroxymethyl-PGF-type compound. The synthetic route for the compounds used in the present invention is not limited to the above one and may vary using different protecting, reducing and/or oxidizating methods.

Since the compounds used in the present invention exhibit a potent uterine contracting activity, they can be used for a medicament or a pharmaceutical composition for effecting uterine contraction and in particular for therapeutic abortion, artificial interruption of pregnancy and/or contraception, as well as for disengagement of fetus in incomplete abortion, for treatment of bleeding after complete or incomplete abortion, of puerperal bleeding, after-curettage bleeding, metrorrhagia at menses, for stimulation of pains, induction of labor and involution of uterus.

These compounds have an advantage in almost or completely avoiding side effects such as gastro-intestinal contraction when used for the above application.

The compounds used in the present invention may be used as a medicine for animals and human beings and usually applied systemically or locally by the method of oral administration, oral administration by spraying, intravenous injection (including instillation), subcutaneous injection, suppository, spraying, coating, gargling and the like. While the dosage will vary depending on the animal or human patient, age, body weight, symptom to be treated, desired therapeutic effect, administration route, term of treatment and the like, satisfactory effects will be obtained with the dosage of 0.001–500 mg/kg administered in 2 to 4 divided doses a day or as a sustained form.

As solid composition of this invention for oral administration, tablets. troches, buccals capsuled, pills, powders, granules and the like are included. The solid composition containing one or more active substances is mixed with at least an inactive diluent such as lactose, mannitol, glucose, hydrocypropyl cellulose, fine crystalline cellulose, starch, polyvinyl pyrolidone, magnesium aluminate metasilicate. The composition may contain additives other than the inactive diluent, such as lubricants e.g., magnesium stearae, a disintegrator e.g. cellulose calcium gluconates, stabilizers e.g. α-, β- or γ-cyclodextrins, etherated cyclodextrins (e.g. dimethyl-α-, dimethyl-β-, trimethyl-β-, or hydroxypropyl-β-cyclodextrins), branched cyclodextins (e.g. glucosyl- or maltosyl-cyclodextrins), formyl cyclodextrins, sulfur-containing cyclodextrins, misoprotols or phospholipids. Such cyclodextrins may form increase the stability of the compounds. The stability may be often increased by forming lyposome with phospholipids. Tablets and pills may be coated with an enteric or gastroenteric film such as white sugar, gelatin, hydroxypropylcellulose, hydroxypropylmethylcellulose phthalates and the like, if necessary, and furthermore they may be covered with two or more layers. Additionally, the composition may be in the form of capsules made of substance easily absorbed such as gelatin.

Liquid compositions for oral administration include pharmaceutically acceptable emulsions, solutions, suspensions, syrups, elixirs and the like and contain a generally used inactive diluent such as purified water of ethyl alcohol. The composition may contain additives such as wetting agents, suspending agents, sweeteners, flavors, perfumes and preservatives.

The compositions for oral administration may contain one or more active substance.

The composition of the present invention may be sprays which can be prepared according to a well known method. The sprays are particularly suitable for the prevention or treatment of paroxysm of asthma. which may be prepared, for instance, by dispersing effective compounds with the aid of surface active agent into blowing agents such as Flon.

The injection of this invention for non-oral administration includes serile aqueous or nonaqueous solutions, suspensions, and emulsions. Diluents for the aqueous solution or suspension include, for example, distilled water for injection, physiological saline and Ringer's solution. Diluents for the nonaqueous solution and suspention include, for example, propylene glycol, polyethylene glycol, vegetable oils such as olive oil, alcohols such as ethanol and polysorbates. The composition may contain other additives such as preservatives, wetting agents. emulsifying agents, dispersing agents and the like. These are sterilized by filtration through, e.g. a bacteria-retaining filter, compounding with a sterilizer, gas sterilization or radiation sterilization. These can be prepared by producing a sterilized water or a sterilized solvent for injection before use.

Another formulation according to the present invention is the rectal or vaginal suppository. This can be prepared by mixing at least one active compound according to the invention with a suppository base such as cacao butter by body temperature, optionally containing non-ion surfactant for improving absorption.

A more complete understanding of the present invention can be obtained by reference to the following Examples which are provided herein for purpose of illustration only and are not intended to limit the scope of the invention.

PREPARATION OF THE COMPOUNDS

Example 1

Synthesis of dimethyl-(3-m-trifluoromethylphenoxy-2-oxopropyl)-phosphonate:

Chloroacetic acid (9.45 g) dissolved in aqueous sodium hydroxide solution (4 g/50 ml) was added at room temperature into trifluorocresol (8.1 g) in aqueous sodium hydroxide (2 g/30 ml). The reaction solution was heated up to 110 °C. for 28 hr with stirring. After cooled, the reaction solution was acidified with dil. hydrochloric acid to generate a white precipitation, which was filtered off. The filtered precipitate was washed with water, and dissolved into ethyl acetate. The ethyl acetate solution was dried over MgSO$_4$. Removal of the solvent from the solution left a crude product, which was chromatographed on silica-gel. Methyl m-trifluoromethylphenoxyacetate was obtained.

Yield: 7.3 g n-Buthyllithium (1.6-M) was added dropwise to dimethyl methylphosphonate (7.8 g) in dry THF (200 ml) cooled at −78 °C. under argon. The reaction was stirred at the temperature for 40 min.

Methyl m-trifluoromethylphenoxyacetate (7.3 g) in dry THF solution was added to the above reaction solution at −78° C. and the reaction was kept at −78 °C. for 4 hr. Acetic acid (4 g) was added. After warmed to the room temperature, the most of the solvent from the reaction was removed in vacuo, and the residue was taken into ethyl acetate. The ethyl acetate extract was washed with water, and dried over MgSO$_4$. Removal of the solvent from the extract left a crude product, which was chromatographed on silica-gel to yield dimethyl (3-m-trifluoromethylphenyoxy-2-oxopropyl)-phosphonate.

Yield: 8.3 g

Example 2

Synthesis of 1S-2-oxa-3-oxo-6R-(3-oxo-4-m-trifluoromethylphenoxy-1-trans-butenyl)-7R-p-phenylbenzoyloxy-cis-bicyclo[3,3,0]octane (23):

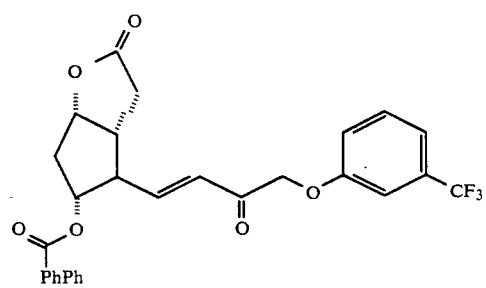

Dimethyl (3-m-trifluoromethylphenoxy-2-oxopropyl)phosponate (2.3 g) in dry THF (20 ml) was added at room temperature to NaH (60 %, 0.282 g) in THF (50 ml), and the reaction mixture was stirred for 30 min. To the above reaction mixture was added the aldehyde (22) in THF (30 ml) obtained after Collins oxidation of (−)-Corey lactone (21) (2.5 g). After the usual work-up, α,β-unsaturated ketone (23) was obtained.

Example 3

Synthesis of 1S-2-oxa-3-oxo-6R-(3-oxo-4-m-trifluoromethylphenoxybutyl)-7R-p-phenylbenzoyloxy-cis-bicyclo[3,3,0]octane (24):

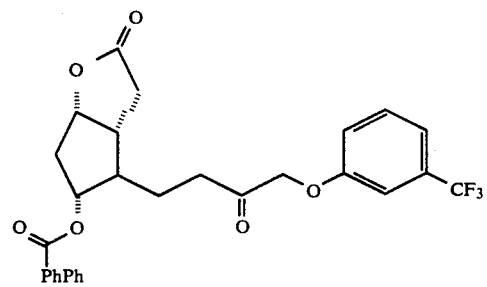

The above mentioned, α,β-unsaturated ketone (23) was hydrogenated with 5% Pd-C and hydrogene.
Yield: 1.68 g

Example 24

Synthesis of 1S-2-oxa-3-oxo-6R-(3R,S-hydroxy-4-m-trifluoromethyl-phenoxybutyl)-7R-p-phenylbenzoyloxy-cisbicyclo[3,3,0] octane (25):

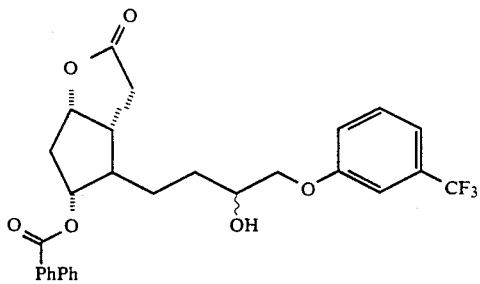

Saturated ketone (24) (1.68 g) was reduced with NaBH₄ (0.027 g) in methanol (25 ml). The crude product obtained after the usual work-up was chromatogrophed on silica-gel with ethyl acetate-hexane (3:2–2:1).

Yield: 1.58 g

Example 5

Synthesis of 1S-2-oxa-3-oxo-6R-(3R,S-t-butyldimethylsilyloxy-4-m-trifluoromethylphenoxybutyl)-7R-p-phenyylbenzoyloxy-cis-bicyclo[3,3,0]octane (26):

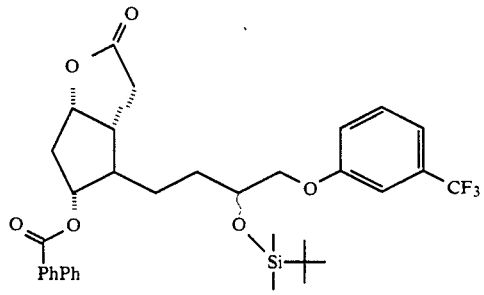

Alcohol (25) (1.58 g) in DMF (3 ml) was treated with t-butyldimethylsilyl chloride (1.20 g) and imidazol (1.08 g). The crude product obtained after usual work-up was chromatographed on silica-gel with ethyl acetate-hexane 1:2).

Yield: 1.98 g

Example 6

Synthesis of 1S-2-oxa-3-oxo-6R-(3R,S-t-butyldimethylsilyloxy-4-m-trifluoromethylphenoxybutyl)-7R-hydroxy-cis-bicyclo[3,3,0]octone (27):

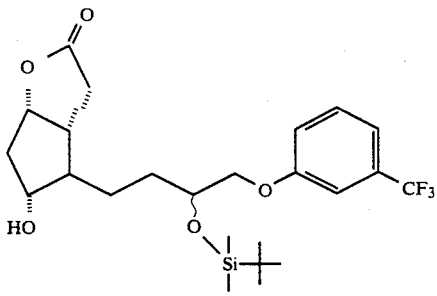

Silylether (26) (1.98 g) was treated with K₂CO₃ (0.383 g) in dry methanol (40 ml) at room temperature for 5 hr. After addition of acetic acid (0.333 g), the usual work-up was done on the reaction mixture to yield the crude product, which, on chromatography over silica-gel (ethyl acetate : hexane = 1:2) gave 1.21 g purified compound (27).

Example 7

Synthesis of 1S-2-oxa-3R,S-hydroxy-6R-(3R,S-t-butyldimethylsilyloxy-4-m-trifluoromethylphenoxybutyl)-7R-(2-tetrapyranyl)oxy-cis- bicyclo[3,3,0]octane (28):

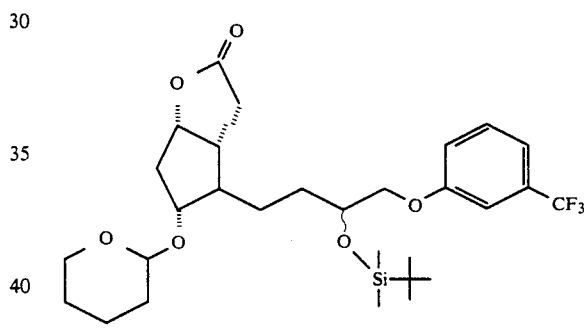

Alcohol (27) (1.21 g) was converted to the corresponding tetrapyranylether(28) with dihydropyrane and catalitic amount of p-toluenesulfonic acid in dichloromethane. Yield: 1.40 g The above mentioned tetrapyranylether (28) (1.40 g) was reduced at −78 ° C. with DIBAL-H (1.5 mole, 2.9 ml) in toluene to the corresponding lactol (29).

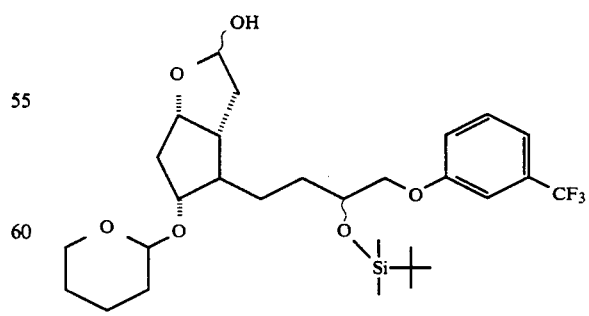

Example 8

Synthesis of 13,14-dihydro-15R,S-t-butyldimethylsilyloxy-16-desbutyl-16-m-trifluoromethylphenoxy- 11R-(2-tetrapyranyl)oxy-PGF (30) and its methyl ester (31):

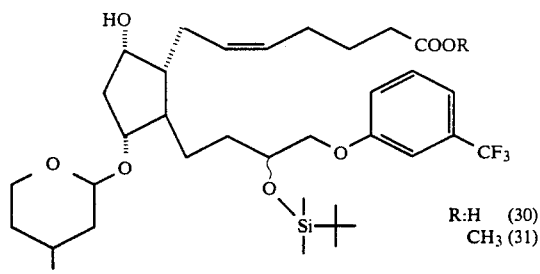

R:H (30)
CH₃ (31)

Lactol (29) in DMSO was added to the ylide generated from (4-carboxybutyl)triphyenylphosphonium bromide (4.33 g) and methylsulfinyl carbanion from NaH (60%, 0.781 g) and DMSO. The reaction solution was stirred for 3 hr. After the usual work-up, 13,14-dihydro-15R,S-t-butyldimethylsilyloxy-16-desbutyl-16-m-trifluoromethylphenoxy-11R-(2-tetrapyranyl)-oxy-PGF (30) was obtained.

The crude product was converted with diazomethane to 13,14-dihydro-15R,S-t-butyldimethylsilyloxy-16-desbutyl16-m-trifluoromethylphenoxy-11R-(2-tetrapyranyl)oxy-PGF$_{2\alpha}$ methyl ester (31).

Example 10

Synthesis of 13,14-dihydro-15R,S-hydroxy-16-desbutyl-16-m-trifluoromethylphenoxy-11R-(2-tetrapyranyl)oxy-PGF$_{2\alpha}$ methyl ester (32).

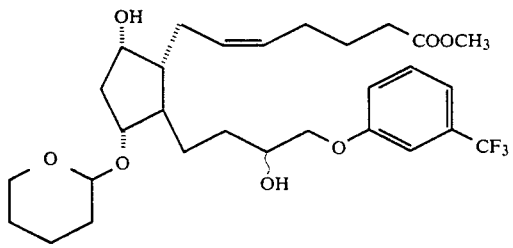

Methyl ester (31) (0.67 g) in THF was treated with tetrabutylammonium fluoride (1-M, 1 ml) at room temperature for 12 hr. The crude product obtained after the usual work-up was chromatographed on silica-gel (32).
Yield: 0.227 g Example 11

Synthesis of 13,14-dihydro-15-keto-16-desbutyl-16-m-trifluoromethylphenoxy-11R-(2-tetrapyranyl)oxy-PGE$_2$ methyl ester (33):

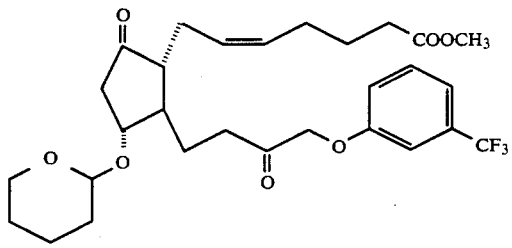

Diol (32) (0.227 g) was oxidized with Jones reagent in acetone at −78 ° C. The crude product obtained after the usual work-up was chromatographed on silica-gel to yield diketone (33).
Yield: 0.135 g Example 12

Synthesis of 13,14-dihydro-15-keto-16-desbutyl-16-m-trifluoromethyl-phenoxy-PGE$_2$ methyl ester (34):

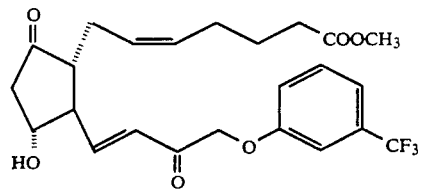

Diketone (33) (0.135 g) was treated with the mixed solvent of acetic acid-water-THF (3:1:1, 15 ml) at 40°–45 ° C. for 4 hr. The crude product obtained after the usual work-up was chromatographed on silica-gel to yield 13,14-dihydro-15-keto-16-desbutyl-16-m-trifluoromethylphenoxy-PGE$_2$ methyl ester (34). Yield: 0.086 g Example 13

Synthesis of 13,14-dihydro-15-keto-16-desbutyl-16-m-trifluoromethylphenoxy-PGE$_2$ (37): 13,14-dihydro-15R,S-hydroxy-16-desbutyl-16-m-trifluoromethyl-phenoxy-11R-(2-tetrapyranyl)oxy-PGF$_{2\alpha}$ (35):

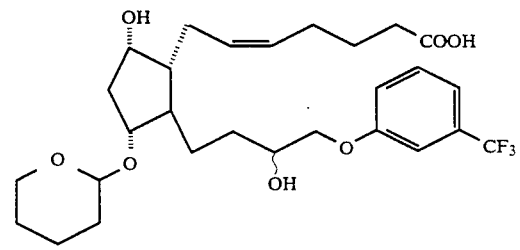

The carboxylic acid (34) (0.327 g) in THF was treated with tetrabutylammonium fluoride (1-M, 0.55 ml) for 2 days. The crude product obtained after the usual work-up was chromatographed on silica-gel to give (35).
Yield: 0.152g.

Example 14

Synthesis of 13,14-dihydro-15-keto-16-desbutyl-16-m-trifluoromethyl-phenoxy-11R-(2-tetrapyranyl)oxy-PGE$_2$ (36):

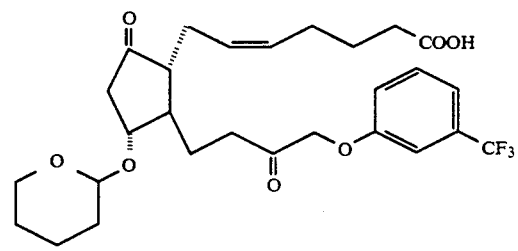

Diol (35) (0.152 g) was oxidized with Collins reagent to the corresponding diketone (36).
Yield: 0.103 g

Example 15

Synthesis of 13,14-dihydro-15-keto-16-desbutyl-16-m-trifluoromethyl-phenoxy-PGE$_2$ (37):

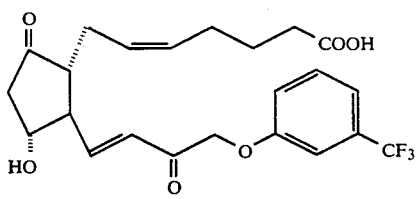

Diketone (36) (0.103 g) was treated with the mixed solvent of acetic acid-water-THF (3:1:1, 20 ml) at 35-°40 ° C. for 3.5 hr. The crude product obtained after the usual work-up was chromatographed on silica-gel to yield 13,14-dihydro-15-keto-16-desbutyl-16-m-trifluoromethylphenoxy-PGE$_2$ (37).

Yield: 0.0373 g.

FORMULATIONS

Formulation Example 1

Into methanol (10ml) was dissolved 13,14-dihydro-15-keto-16-desbutyl-16-m-trifluoromethylphenoxy-PGF$_{2\alpha}$ methyl ester (50mg) and the produced solution was mixed with mannitol (18.5g). The mixture was passed through a sieve (pore size: 30mm), driex at 30° C. for 90 minutes and then sieved again. The produced powders were mixed with micro-fine silica (Aerosil, 200g) and the mixture was filled into No.3 hard gelatine capsules (100). The capsules were enteric capsules containing 0.5mg 16-desbutyl-13,14-dihydro-15-keto-16-m-trifluoromethylphenoxy-PGF$_{2\alpha}$ methyl ester per a capsule.

| Formulation Example 2 (Powders for injection) | |
| --- | --- |
| | (Parts by weight) |
| 13,14-dihydro-15-keto-16-desbutyl-16-m-trifluoromethylphenoxy-PGF$_{2\alpha}$ metyl ester | 1 |
| Tween 80 | 0.1 |
| mannitol | 5 |
| distilled water | 0.4 |

The above ingredients were mixed, stirred, sterilized, filtered and lyophilized to give powders for injection.

| Formulation Example 3 (Injectable solution) | |
| --- | --- |
| | (Parts by weight) |
| 13,14-dihydro-15-keto-16-desbutyl-16-m-trifluoromethylphenoxy-PGF$_{2\alpha}$ metyl ester | 0.2 |
| non-ion surfactant | 2 |
| distilled water | 98 |

The above ingredients were mixed and sterilized to give and injectable solution.

| Formulation Example 4 (Powders for oral administration) | |
| --- | --- |
| | (Parts by weight) |
| 13,14-dihydro-15-keto-16-desbutyl-16-m-trifluoromethylphenoxy-PGF$_{2\alpha}$ metyl ester | 5 |
| light anhydrous silicic acid | 5 |
| Abicel | 20 |
| lactose | 70 |

The above ingredients were mixed to give powders for oral administration.

| Formulation Example 5 (Soft gelatine capsules) | |
| --- | --- |
| | (Parts by weight) |
| 13,14-dihydro-15-keto-16-desbutyl-16-m-trifluoromethylphenoxy-PGF$_{2\alpha}$ metyl ester | 1 |
| light anhydrous silicic acid | 899 |
| Panasate | 20 |

The above ingredients were mixed and filled in soft gelatine capsules.

In the above formulation ,examples, the active ingredient can be replaced by any other compound within the compounds used in the invention.

BIOLOGICAL TESTS

Test Example 1

Uterine contraction

An estrous rat (female, 150g) was used as test animals. The rat was sacrificed by bleeding and uterus was extirpated. A section of about 2.0cm was cut off and hung in a Magnus tube containing Tyrode solution or Beauvillain solution.

The section of uterus was held for about 5 minutes until it because stable and then contracted several times by administering oxytocin (1 mU). After stable contraction was obtained, the section received test compounds. Contractions obtained by the test compounds were expressed as a ratio to the contraction by oxytocin which was taken as 100%. The results are shown in Table 1 (15-keto-PGE derivatives) and Table 2 (15-keto-PGF derivatives).

TABLE 1

| Test Compound | Dose (M) | Contraction (%) |
| --- | --- | --- |
| X-1 | $3 \times 10^{-5}$ | 80 |
| X-2 | $1 \times 10^{-4}$ | 50 |
| X-3 | $1 \times 10^{-4}$ | 50 |
| X-4 | $1 \times 10^{-4}$ | 66 |
| X-5 | $3 \times 10^{-5}$ | 88 |
| X-6 | $3 \times 10^{-5}$ | 85 |
| X-7 | $1 \times 10^{-4}$ | 50 |
| X-8 | $3 \times 10^{-5}$ | 79 |
| X-9 | $1 \times 10^{-4}$ | 86 |
| X-10 | $1 \times 10^{-4}$ | 60 |
| X-11 | $1 \times 10^{-4}$ | 81 |
| X-12 | $1 \times 10^{-4}$ | 50 |
| X-13 | $3 \times 10^{-5}$ | 48 |
| X-14 | $3 \times 10^{-5}$ | 68 |
| X-15 | $1 \times 10^{-5}$ | 82 |
| X-16 | $3 \times 10^{-7}$ | 53 |
| X-17 | $1 \times 10^{-5}$ | 78 |
| X-18 | $3 \times 10^{-5}$ | 79 |
| X-19 | $1 \times 10^{-4}$ | 73 |
| X-20 | $1 \times 10^{-4}$ | 83 |
| X-21 | $1 \times 10^{-4}$ | 71 |
| X-22 | $1 \times 10^{-5}$ | 83 |
| X-23 | $1 \times 10^{-4}$ | 50 |
| X-24 | $1 \times 10^{-6}$ | 87 |
| X-25 | $3 \times 10^{-6}$ | 64 |
| X-26 | $1 \times 10^{-5}$ | 89 |
| X-27 | $1 \times 10^{-4}$ | 50 |
| X-28 | $1 \times 10^{-4}$ | 50 |

TABLE 1-continued

| | | |
|---|---|---|
| X-29 | $1 \times 10^{-5}$ | 64 |
| X-30 | $1 \times 10^{-5}$ | 56 |
| X-31 | $1 \times 10^{-4}$ | 50 |
| X-32 | $1 \times 10^{-4}$ | 50 |
| X-33 | $1 \times 10^{-5}$ | 84 |
| X-34 | $1 \times 10^{-7}$ | 73 |
| X-35 | $1 \times 10^{-5}$ | 65 |
| X-36 | $1 \times 10^{-5}$ | 80 |
| X-37 | $1 \times 10^{-5}$ | 80 |
| X-38 | $3 \times 10^{-5}$ | 79 |
| X-39 | $1 \times 10^{-6}$ | 80 |
| X-40 | $1 \times 10^{-6}$ | 34 |
| X-41 | $1 \times 10^{-6}$ | 63 |
| X-42 | $1 \times 10^{-6}$ | 81 |
| X-43 | $1 \times 10^{-6}$ | 32 |
| X-44 | $3 \times 10^{-6}$ | 73 |

X-1: 13,14-dihydro-15-keto-$PGE_1$ ethyl ester
X-2: 13,14-dihydro-15-keto-$\Delta^2$-$PGE_1$
X-3: 13,14-dihydro-6,15-diketo-$PGE_1$ ethyl ester
X-4: ±13,14-dihydro-6,15-diketo-$PGE_1$ ethyl ester
X-5: 13,14-dihydro-6,15-diketo-$PGE_1$ n-butyl ester
X-6: 13,14-dihydro-6,15-diketo-16R,S-methyl-$PGE_1$ methyl ester
X-7: 13,14-dihydro-6,15-diketo-16R,S-methyl-$PGE_1$ ethyl ester
X-8: 13,14-dihydro-6,15-diketo-16,16-dimethyl-$PGE_1$ ethyl ester
X-9: 13,14-dihydro-6,15-diketo-16R,S-fluoro-$PGE_1$ ethyl ester
X-10: 13,14-dihydro-6,15-diketo-19-methyl-$PGE_1$ methyl ester
X-11: 13,14-dihydro-6,15-diketo-19-methyl-$PGE_1$ ethyl ester
X-12: 13,14-dihydro-6,15-diketo-11-dehydroxy-11R-hydroxymethyl-19-methyl-$PGE_1$ methyl ester
X-13: 13,14-dihydro-6,15-diketo-20-methyl-$PGE_1$ ethyl ester
X-14: 13,14-dihydro-6,15-diketo-11-dehydroxy-11R-methyl-$PGE_1$ ethyl ester
X-15: 13,14-dihydro-6,15-diketo-16R,S-fluoro-11-dehydroxy-11R-methyl-$PGE_1$ ethyl ester
X-16: 13,14-dihydro-15-keto-$PGE_2$
X-17: 13,14-dihydro-15-keto-$PGE_2$ methyl ester
X-18: 13,14-dihydro-15-keto-$PGE_2$ ethyl ester
X-19: 13,14-dihydro-15-keto-3R,S-methyl-$PGE_2$ methyl ester
X-20: 13,14-dihydro-15-keto-16R,S-methyl-$PGE_2$ methyl ester
X-21: 13,14-dihydro-15-keto-3R,S,16R,S-dimethyl-$PGE_2$ methyl ester
X-22: 13,14-dihydro-15-keto-16,16-dimethyl-$PGE_2$ ethyl ester
X-23: 13,14-dihydro-15-keto-16R,S-hydroxy-$PGE_2$ ethyl ester
X-24: 13,14-dihydro-15-keto-16R,S-fluoro-$PGE_2$
X-25: 13,14-dihydro-15-keto-16R,S-fluoro-$PGE_2$ methyl ester
X-26: 13,14-dihydro-15-keto-16R,S-fluoro-$PGE_2$ ethyl ester
X-27: 13,14-dihydro-15-keto-16R,S-fluoro-11-dehydroxy-11R-methyl-$PGE_2$ ethyl ester
X-28: 13,14-dihydro-15-keto-11-dehydroxy-11R-methyl-$PGE_2$ ethyl ester
X-29: 13,14-dihydro-15-keto-16,16-dimethyl-20-methoxy-$PGE_2$ methyl ester
X-30: 13,14-dihydro-15-keto-20-ethyl-$PGE_2$ ethyl ester
X-31: 13,14-dihydro-15-keto-20-ethyl-11-dehydroxy-11R-methyl-$PGE_2$ methyl ester
X-32: 13,14-dihydro-15-keto-20-n-propyl-$PGE_2$ methyl ester
X-33: 15-keto-16R,S-fluoro-$PGE_2$ methyl ester
X-34: $PGE_2$
X-35: $PGE_2$ methyl ester
X-36: 13,14-dihydro-15-keto-16R,S-fluoro-20-methyl-$PGE_2$ methyl ester
X-37: 13,14-dihydro-15-keto-$\Delta^2$-$PGE_1$
X-38: 13,14-dihydro-15-keto-20-methyl-$PGE_1$
X-39: 15-keto-16R,S-fluoro-$PGE_2$
X-40: 13,14-dihydro-15-keto-16R,S-fluoro-$PGE_1$
X-41: 13,14-dihydro-15-keto-16,16-difluoro-$PGE_2$ methyl ester
X-42: 13,14-dihydro-15-keto-16,16-difluoro-$PGE_2$
X-43: 13,14-dihydro-15-keto-16-desbutyl-16-m-trifluoro-methylphenoxy-$PGE_2$
X-44: 13,14-dihydro-15-keto-16-desbutyl-16-m-trifluoro-methylphenoxy-$PGE_2$

TABLE 2

| Test Compound | Dose (M) | Contraction (%) |
|---|---|---|
| Y-1 | $3 \times 10^{-6}$ | 84 |
| Y-2 | $3 \times 10^{-5}$ | 98 |
| Y-3 | $1 \times 10^{-4}$ | 78 |
| Y-4 | $1 \times 10^{-4}$ | 50 |
| Y-5 | $1 \times 10^{-4}$ | 91 |
| Y-6 | $3 \times 10^{-7}$ | 89 |
| Y-7 | $3 \times 10^{-6}$ | 70 |
| Y-8 | $3 \times 10^{-6}$ | 82 |
| Y-9 | $1 \times 10^{-4}$ | 50 |
| Y-10 | $3 \times 10^{-6}$ | 42 |
| Y-11 | $3 \times 10^{-7}$ | 92 |
| Y-12 | $1 \times 10^{-5}$ | 85 |
| Y-13 | $1 \times 10^{-4}$ | 50 |
| Y-14 | $1 \times 10^{-4}$ | 50 |
| Y-15 | $3 \times 10^{-5}$ | 80 |
| Y-16 | $3 \times 10^{-6}$ | 64 |
| Y-17 | $1 \times 10^{-5}$ | 88 |
| Y-18 | $3 \times 10^{-5}$ | 89 |
| Y-19 | $1 \times 10^{-4}$ | 97 |
| Y-20 | $1 \times 10^{-4}$ | 50 |
| Y-21 | $1 \times 10^{-4}$ | 50 |
| Y-22 | $1 \times 10^{-4}$ | 50 |
| Y-23 | $1 \times 10^{-4}$ | 50 |
| Y-24 | $3 \times 10^{-7}$ | 92 |
| Y-25 | $1 \times 10^{-5}$ | 95 |
| Y-26 | $3 \times 10^{-5}$ | 81 |
| Y-27 | $3 \times 10^{-5}$ | 70 |
| Y-28 | $3 \times 10^{-8}$ | 64 |
| Y-29 | $1 \times 10^{-7}$ | 52 |
| Y-30 | $3 \times 10^{-6}$ | 67 |

Y-1: 13,14-dihydro-15-keto-$PGF_{2\alpha}$
Y-2: 13,14-dihydro-15-keto-$PGF_{2\alpha}$ methyl ester
Y-3: 13,14-dihydro-15-keto-$PGF_{2\alpha}$ ethyl ester
Y-4: 13,14-dihydro-15-keto-9$\beta$-$PGF_{2\alpha}$ methyl ester
Y-5: 13,14-dihydro-15-keto-16,16-dimethyl-$PGF_{2\alpha}$ ethyl ester
Y-6: 13,14-dihydro-15-keto-16R,S-fluoro-$PGF_{2\alpha}$
Y-7: 13,14-dihydro-15-keto-16R,S-fluoro-$PGF_{2\alpha}$ methyl ester
Y-8: 13,14-dihydro-15-keto-16,16-difluoro-$PGF_{2\alpha}$ methyl ester
Y-9: 13,14-dihydro-15-keto-16R,S-fluoro-11-dehydroxy-11R-methyl-$PGF_{2\alpha}$ ethyl ester
Y-10: 13,14-dihydro-15-keto-16R,S-fluoro-20-methyl-$PGF_{2\alpha}$ methyl ester
Y-11: 13,14-dihydro-15-keto-20-ethyl-16R,S-fluoro-$PGF_{2\alpha}$
Y-12: 13,14-dihydro-15-keto-20-ethyl-16R,S-fluoro-$PGF_{2\alpha}$ methyl ester
Y-13: 13,14-dihydro-15-keto-20-ethyl-16R,S-fluoro-11-dehydroxy-11R-methyl-$PGF_{2\alpha}$ methyl ester
Y-14: 13,14-dihydro-15-keto-20-methoxy-$PGF_{2\alpha}$ methyl ester
Y-15: 13,14-dihydro-15-keto-20-methyl-$PGF_{2\alpha}$ methyl ester
Y-16: 13,14-dihydro-15-keto-20-ethyl-$PGF_{2\alpha}$
Y-17: 13,14-dihydro-15-keto-20-ethyl-$PGF_{2\alpha}$ methyl ester
Y-18: 13,14-dihydro-15-keto-20-ethyl-$PGF_{2\alpha}$ ethyl ester
Y-19: 13,14-dihydro-15-keto-20-ethyl-$PGF_{2\alpha}$ isopropyl ester
Y-20: 13,14-dihydro-15-keto-20-ethyl-$PGF_{2\alpha}$ n-butyl ester
Y-21: 13,14-dihydro-15-keto-20-ethyl-11-dehydroxy-11R-methyl-$PGF_{2\alpha}$ methyl ester
Y-22: 13,14-dihydro-15-keto-20-n-propyl-$PGF_{2\alpha}$ methyl ester
Y-23: 13,14-dihydro-15-keto-20-n-butyl-$PGF_{2\alpha}$ methyl ester
Y-24: 13,14-dihydro-15-keto-16-desbutyl-16-m-trifluoromethylphenoxy-$PGF_{2\alpha}$ methyl ester
Y-25: 15-keto-16R,S-fluoro-$PGF_{2\alpha}$ methyl ester
Y-26: 13,14-dihydro-15-keto-$PGF_{1\alpha}$ ethyl ester
Y-27: 13,14-dihydro-15-keto-20-ethyl-$PGF_{1\alpha}$ methyl ester
Y-28: $PGF_{2\alpha}$
Y-29: 13,14-dihydro-15-keto-16-desbutyl-16-m-trifluoro-methylphenoxy-$PGF_{2\alpha}$
Y-30: 15-keto-17S-methyl-$PGF_{2\alpha}$ ethyl ester Test Example 2

Intestinal contraction ... Reference example

A section was cut off from ileun of a Wistar rat (male) and hung in a Magnus tube. The section was contracted several times by administering acetylcholine ($1 \times 10^{-6}$ g/ml) and received test compounds after giving two or more contractions of the same intensity. Contractions obtained by the test compounds were expressed as a ratio to the contraction by acetylcholine ($1 \times 10^{-6}$ g/ml) which was taken as 100%, and $EC_{50}$ values were calculated as a concentrations for 50% contraction. The results are shown in Table 3.

Test Example 3

Ocular hypertension ... Reference example

Japanese white rabbits (male) were used as test animals. Intraocula pressure was measured under 0.4% topical oxybeprocaine hydrochloride anestheria using a pneumatonometer. Test compounds were dissolved in ethanol, diluted at least by 50 times with the physiological saline and administered at a dose of 1 mg/kg into the auricular vein of the rabbit. The results are shown in Table 3.

TABLE 3

| Test compound | intestinal contraction* | ocular hypertension** |
|---|---|---|
| X-17 | − | − |
| Y-19 | − | − |
| Y-2 | − | |
| PGE$_2$ | + | + |
| PGF$_{2\alpha}$ | ++ | + |

*++: EC$_{50}$ < $10^{-7}$
+: $10^{-7}$ ≧ EC$_{50}$ ≧ $10^{-6}$
−: $10^{-6}$ < EC$_{50}$

**+: Increase in intraocular pressure is observed in at least one of three animals.
−: No increase was observed in intraocula pressure.

From the above results, it can be concluded that the compounds used in the test exhibit specific uterine contracting activety without accompanying intestinal contraction and ocular hypertension which are caused by 15-hydroxy typed PGEs or PGFs.

Test Example 4

Anti-pregnancy

Golden hamsters (male, 9 weeks) subcutaneously received test compounds on day 4, 5 and 6 of pregnancy counted from the day (taken as day 1) on which spermia were observed in vaginal smear. On day 8, animals were sacrificed and maintenace or interruption of pregnancy was decided by the presence or absence of intrauterine nidation signs. Values of ED$_{50}$ for anti-pregnancy were calculated as the doses at which interruption of pregnancy occurs in 50% of the treated animals. The results are shown in Table 4.

Test Example 5

Intestinal contraction ... Reference example

A section was cut off from ilem of a Wistar rat (male) and hung in a Magnus tube. The section was contracted several times by administering acetylcholine ($1 \times 10^{-6}$ g/ml) and received test compounds after giving two or more contractions of the same intensity. Contractions obtained by the test compounds were expressed as a ratio to the contraction by acetylcholine ($1 \times 10^{-6}$ g/ml) which was taken as 100%, and EC$_{50}$ values were calculated as a concentrations for 50% contraction. The results are shown in Table 4.

TABLE 4

| Test compound | Anti-pregnancy action | intestinal contraction action* |
|---|---|---|
| Y-24 | 20 | − |
| Y-29 | 13 | − |
| Y-28 | 14 | ++ |

*++: ED$_{50}$ ≦ $10^{-7}$
+: $10^{-7}$ < ED$_{50}$ ≦ $10^{-6}$
−: $10^{-6}$ < ED$_{50}$

Similarly, 13,14-dihydro-15-keto-PGF$_{2\alpha}$ methyl ester exhibited the anti-pregnancy action with ED$_{50}$ of 50 to 500 μg/hamster and without intestinal contraction.

Also, when 13,14-dihydro-15-keto-16-desbutyl-16-m-trifluoromethylphenoxy-PGE$_2$ was administered a dose of 500 μg/hamster, no sign of nidation was observed in 2 out 6 animals and death of fetus was observed in 4 out 6 animals, indicating it has the anti-pregnancy action.

From the above results, it can be concluded that the comopunds used in the test exhibit potent anti-pregnancy activity without accompanying intestinal contraction as seen in the treatment with natural PGF$_{2\alpha}$.

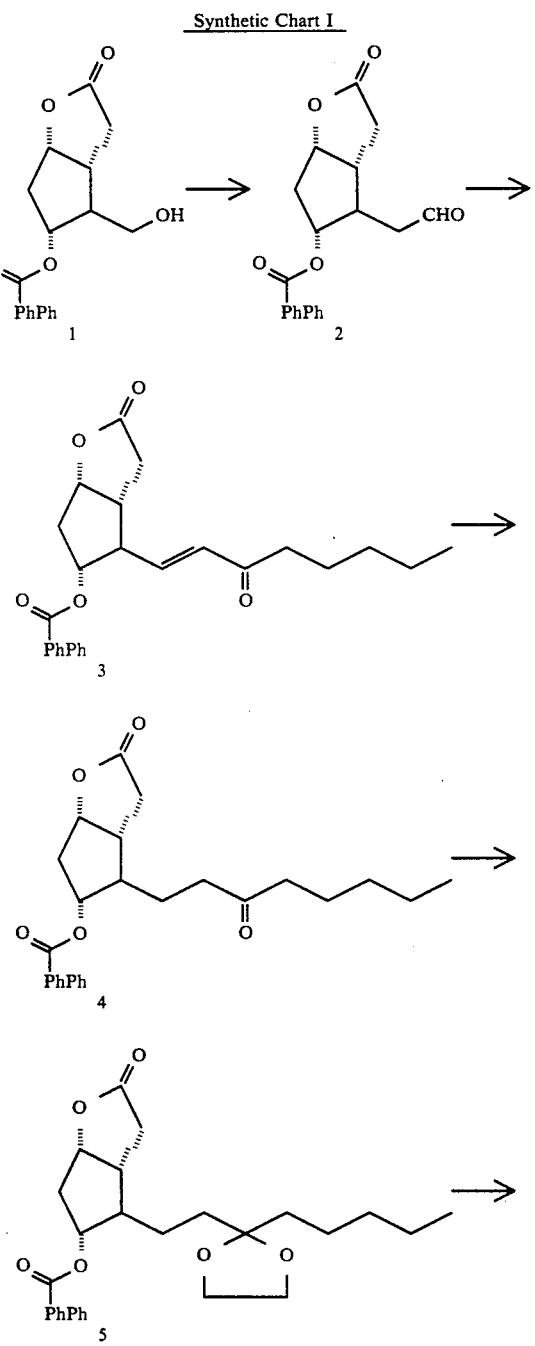

Synthetic Chart I

-continued
Synthetic Chart I
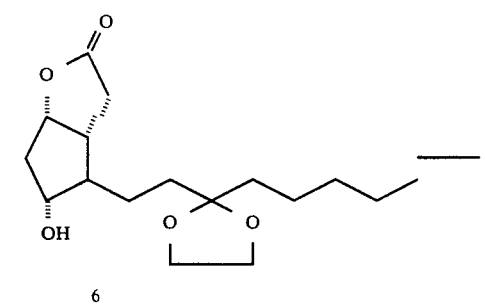
6
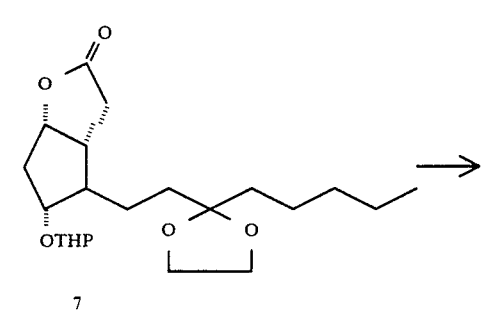
7
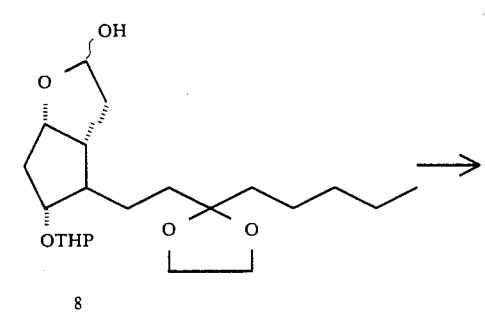
8
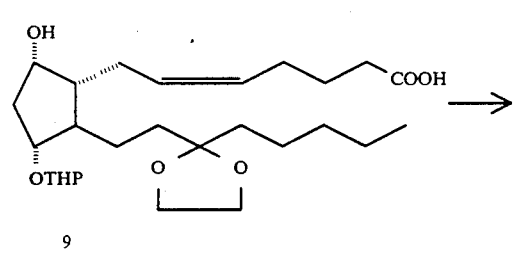
9
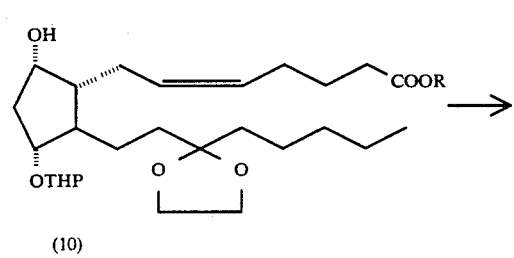
(10)
-continued
Synthetic Chart I
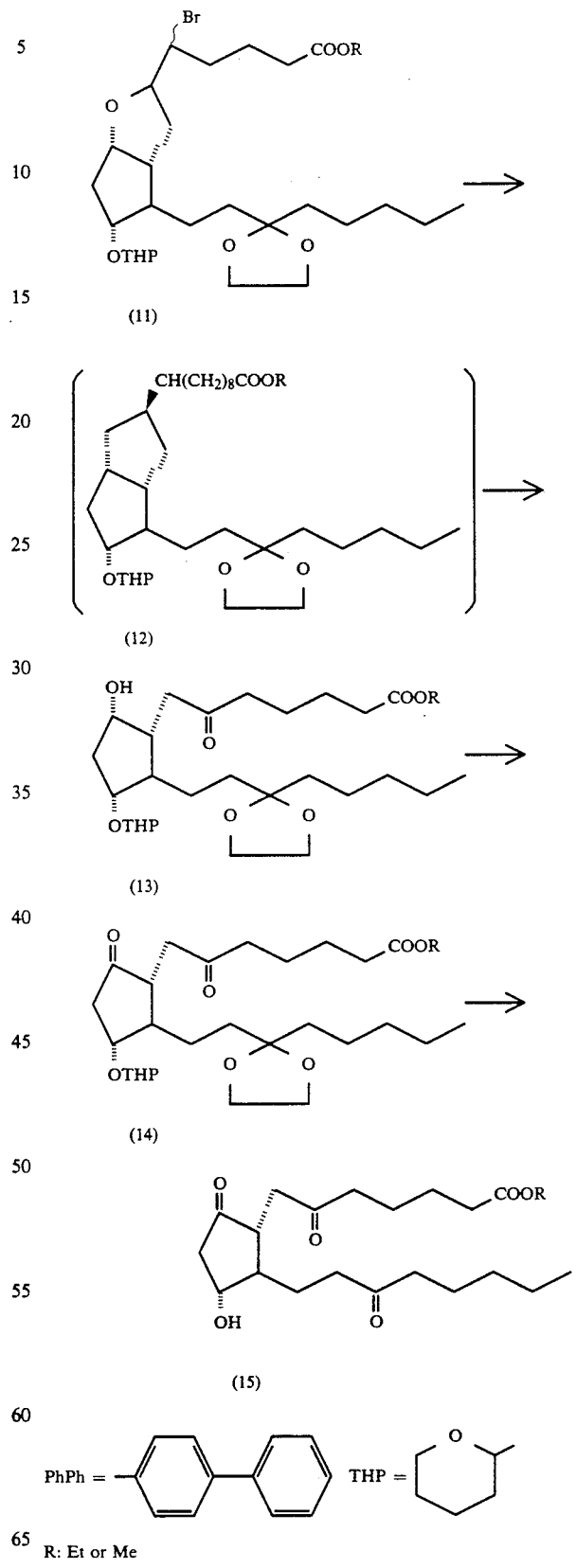
PhPh = —⟨C₆H₄–C₆H₅⟩   THP = tetrahydropyranyl
R: Et or Me

Synthetic Chart II
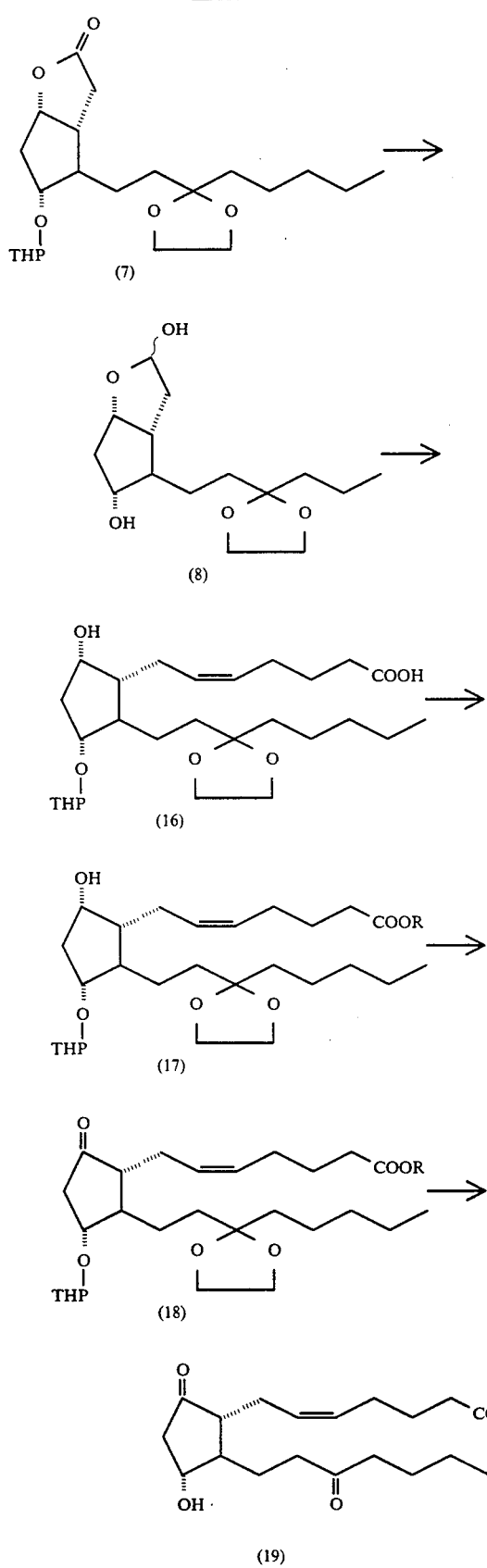
Synthetic Chart III
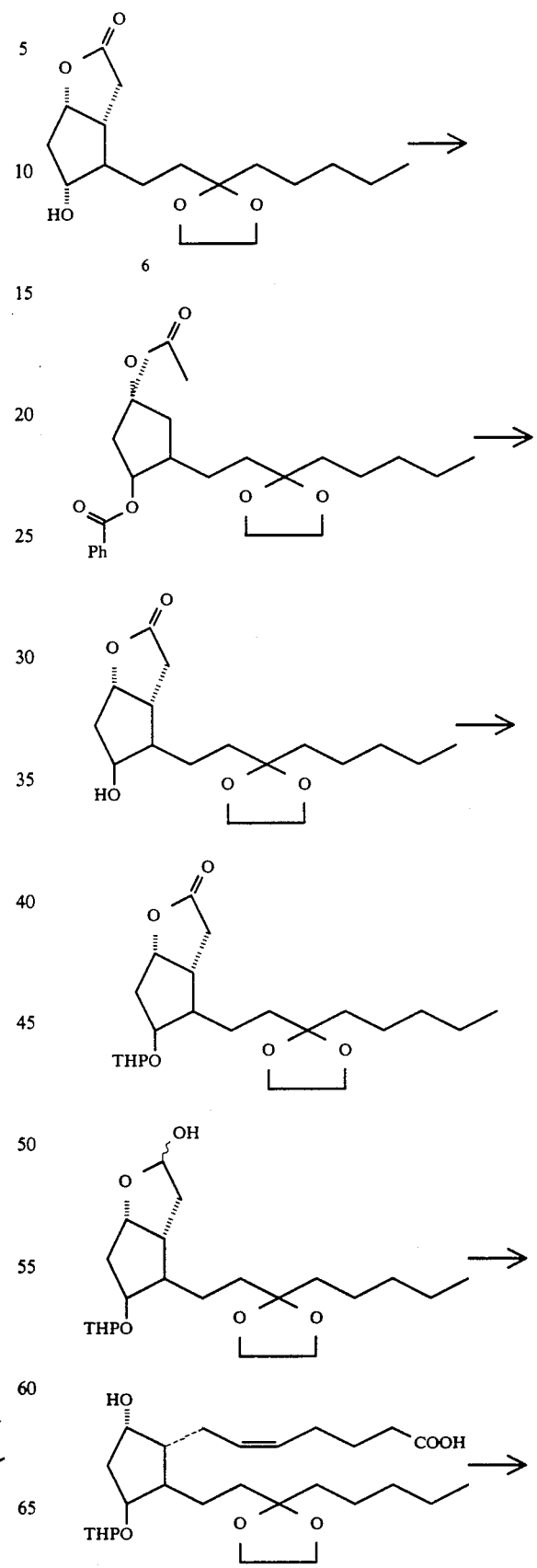

-continued
Synthetic Chart III

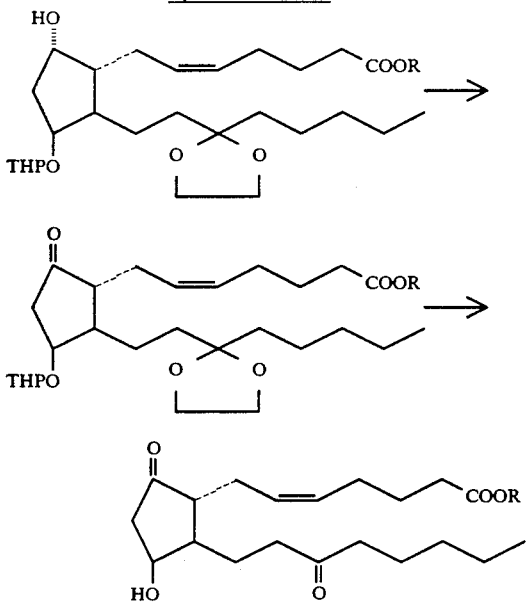

What is claimed is:

1. A method of inducing uterine contraction which comprises the step of
administering, to a subject in need of such contraction, a uterine-contractionally effective amount of a prostanoic acid derivative of general formula (I)

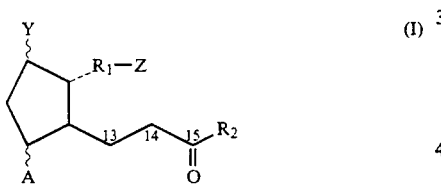

wherein
A is a hydroxy group, a lower alkyl group, or a hydroxy(lower)-alkyl group;
Y is a hydroxy group or an oxo group;
Z is a —COOH group or a functional derivative of a —COOH group;
$R_1$ is a straight or branched chain hydrocarbyl group having 1 to 14 carbon atoms; and
$R_2$ is a straight or branched chain hydrocarbyl group having 1 to 11 carbon atoms substituted with hydroxy, halo, lower alkyl, aryl oxy at the 16-position.

2. The method according to claim 1 for interruption of pregnancy.

3. The method according to claim 1, wherein said prostanoic acid derivative has a carboxy (—COOH) group at the free end of α-chain of the prostanoic acid nucleus.

4. The method according to claim 1, wherein said prostanoic acid derivative is a 6,15-diketo-prostaglandin E compound or a 6,15-diketo-prostaglandin F compound.

5. The method according to claim 1, wherein said prostanoic acid derivative is a 16-mono or di(lower)alkylprostaglandin E compound or a 16-mono or di(-lower)alkylprostaglandin F compound.

6. The method according to claim 1, wherein said prostanoic acid derivative is a 16-mono- or di-halo-prostaglandin E compound or a 16-mono- or di-halo-prostaglandin F compound.

7. The method according to claim 1, wherein said prostanoic acid derivative is a 20-(lower)alkylprostaglandin E compound or a 20-(lower)alkyl-prostaglandin F compound.

8. The method according to claim 1, wherein said prostanoic acid derivative is a 13,14-dihydro-15-keto-16-desbutyl- 16-aryloxy-PGE or a 13,14-dihydro-15-keto-16-desbutyl-16-aryloxy-PGF.

9. The method according to claim 8, wherein said prostanoic acid derivative is a 13,14-dihydro-15-keto-16-desbutyl-16 - trifluoromethylphenoxy-PGE or a 13,14-dihydro-15-keto-16-desbutyl-16-trifluoromethylphenoxy-PGF.

10. The method according to claim 1, wherein said prostanoic acid derivative is a 13,14-dihydro-15-keto-17-oxa-PGE or a 13,14-dihydro-15-keto-17-oxa-PGF.

11. The method of claim 1, wherein said prostanoic acid derivative of the general formula (I) is a prostaglandin F compound or a prostaglandin E compound in which $R_2$ is substituted with alkyl.

12. The method of claim 1, wherein said prostanoic acid derivative of the general formula (I) is a prostaglandin F compound or a prostaglandin E compound in which $R_2$ is substituted with halo.

13. A method of inducing uterine contraction which comprises the step of
administering, to a subject in need of such contraction, a uterine-contractionally effective amount of a prostanoic acid derivative of general formula (I)

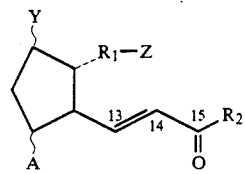

wherein
A is a hydroxy group, a lower alkyl group, or a hydroxy(lower)-alkyl group;
Y is a hydroxy group or an oxo group;
Z is a —COOH group or a functional derivative of a —COOH group;
$R_1$ is a straight or branched chain hydrocarbyl group having 1 to 14 carbon atoms; and
$R_2$ is a straight or branched chain hydrocarbyl group having 1 to 11 carbon atoms substituted with halo at the 16-position.

14. The method according to claim 13 for the interruption of pregnancy.

15. The method according to claim 13, wherein said prostanoic acid derivative has a —COOH group at the free end of the α-chain of the prostanoic acid nucleus.

16. The method according to claim 13, wherein said prostanoic acid derivative is a 6,15-diketo-prostaglandin E compound or a 6,15-diketo-prostaglandin F compound.

17. The method according to claim 13, wherein said prostanoic acid derivative is a 20-(lower)alkyl-prostaglandin E compound or a 20-(lower)alkyl-prostaglandin F compound.

18. The method according to claim 13, wherein said prostanoic acid derivative is a 15-keto-16-desbutyl-16-aryloxy PGE or a 15-keto-16-desbutyl-16-aryloxy PGF.

19. The method according to claim 18 wherein said prostanoic acid derivative is a 13,14-dihydro-15-keto-16-desbutyl-16-trifluoromethyl-phenoxy-PGE or a 13,14-dihydro-15-keto-16-desbutyl-16-trifluoromethyl-phenoxy-PGF.

20. The method according to claim 13 wherein said prostanoic acid derivative is a 15-keto-17-oxa-PGE or a 15-keto-17-oxa-PGF.

21. 13,14-dihydro-15-keto-16-desbutyl-16-trifluoromethyl-phenoxy-prostaglandin $E_2$ in free form, O-protected form, physiologically acceptable salt form or physiologically acceptable and physiologically hydrolyzable ester form thereof.

22. 15-keto-16-desbutyl-16-trifluoromethyl-phenoxy-prostaglandin $E_2$ in free form, O-protected form, physiologically acceptable salt form, or physiologically acceptable and physiologically hydrolyzable ester form thereof.

* * * * *